US012758104B2

(12) United States Patent
Gervaix et al.

(10) Patent No.: US 12,758,104 B2
(45) Date of Patent: Oct. 13, 2026

(54) DEVICE AND METHOD FOR MEASURING PARAMETERS OF A PATIENT

(71) Applicants: UNIVERSITÉ DE GENÈVE, Geneva (CH); HÔPITAUX UNIVERSITAIRES DE GENÈVE, Geneva (CH)

(72) Inventors: Alain Gervaix, Cologny (CH); Alexandre Perez, Prilly (CH)

(73) Assignees: UNIVERSITÉ DE GENÉVE, Geneva (CH); HÔPITAUX UNIVERSITAIRES DE GENÈVE, Geneva (CH)

( * ) Notice: Subject to any disclaimer, the term of this patent is extended or adjusted under 35 U.S.C. 154(b) by 185 days.

(21) Appl. No.: 18/565,748

(22) PCT Filed: May 30, 2022

(86) PCT No.: PCT/EP2022/064524
§ 371 (c)(1),
(2) Date: Nov. 30, 2023

(87) PCT Pub. No.: WO2022/253723
PCT Pub. Date: Dec. 8, 2022

(65) Prior Publication Data

US 2024/0366093 A1 Nov. 7, 2024

(30) Foreign Application Priority Data

Jun. 3, 2021 (EP) .................................... 21177615

(51) Int. Cl.
*A61B 5/0205* (2006.01)
*A61B 5/00* (2006.01)
(Continued)

(52) U.S. Cl.
CPC ...... *A61B 5/02055* (2013.01); *A61B 5/14551* (2013.01); *A61B 5/6823* (2013.01);
(Continued)

(58) Field of Classification Search
CPC ............ A61B 5/02055; A61B 5/14551; A61B 5/6823; A61B 5/6826; A61B 7/02;
(Continued)

(56) References Cited

U.S. PATENT DOCUMENTS

2005/0014999 A1* 1/2005 Rahe-Meyer ............ A61B 7/04
600/323
2017/0185737 A1* 6/2017 Kovacs .............. A61B 5/02416
(Continued)

FOREIGN PATENT DOCUMENTS

WO WO 2020/252317 A1 12/2020

*Primary Examiner* — Eugene T Wu
(74) *Attorney, Agent, or Firm* — Weston R. Gould; DINSMORE & SHOHL LLP

(57) ABSTRACT

The present relates to a device for measuring at least one parameter of a patient, the device comprising a casing equipped with at least one sensor for measuring said parameter of the patient. The device comprises at least three sensors, each sensor being configured for measuring one distinct parameter, said three sensors being chosen among a list comprising at least a temperature sensor to measure a temperature of the patient, a sound sensor to record a body sound of the patient and an oximeter sensor to measure a blood oxygen level of the patient. The three sensors are mounted in the casing so that when the device is in contact with the skin of the patient, at least two distinct parameters, preferably three distinct parameters, are measured simultaneously.

15 Claims, 4 Drawing Sheets

(51) Int. Cl.
*A61B 5/1455* (2006.01)
*A61B 7/02* (2006.01)
*A61B 5/024* (2006.01)

(52) U.S. Cl.
CPC .............. *A61B 5/6826* (2013.01); *A61B 7/02* (2013.01); *A61B 5/024* (2013.01)

(58) Field of Classification Search
CPC ........... A61B 5/024; A61B 5/01; A61B 7/003; A61B 7/04
See application file for complete search history.

(56) References Cited

U.S. PATENT DOCUMENTS

| | | | | |
|---|---|---|---|---|
| 2019/0090814 | A1 | 3/2019 | Lee | |
| 2019/0125270 | A1* | 5/2019 | Deriso | A61B 8/488 |
| 2020/0015774 | A1 | 1/2020 | Hussain | |
| 2022/0218256 | A1* | 7/2022 | Thiagarajan | A61B 5/14532 |
| 2024/0000321 | A1* | 1/2024 | Hanuka | A61B 5/113 |

* cited by examiner

DEVICE AND METHOD FOR MEASURING PARAMETERS OF A PATIENT

CROSS REFERENCE TO RELATED APPLICATIONS

This application is a U.S. national stage under 35 U.S.C. § 371 of PCT/EP2022/064524 filed May 30, 2022, which claims priority to European application number 21177615.8 filed Jun. 3, 2021, the contents of which are hereby incorporated by reference in its entirety.

TECHNICAL FIELD

The present invention relates to a device for measuring at least one parameter of a patient and to computer implemented method for remotely operating said device.

The invention also concerns a method for measuring at least three parameters of a patient by using said device.

BACKGROUND OF THE ART

The diagnosis of respiratory diseases is done by pulmonary auscultation using a stethoscope and functional tests. Currently, the tool that is most frequently used by physicians to perform auscultation is a traditional stethoscope, invented by Dr. Laennec 200 years ago.

However, these examinations require significant expertise and can only be conducted by a physician. It requires strong medical expertise and long training to detect clinical sound by ear.

Various approaches exist to improve the existing auscultation tools and facilitating the acquisition of patient parameters such as chest sound.

One of the most promising and popular approach concerns digital or electronic stethoscopes that allow viewing and recording chest sound.

In this respect, the document Kraman et al., Measurement of Respiratory Acoustic Signals, *Chest*, October 1995 illustrates that a key element of any electronic stethoscopes stands in the microphone. This document describes the effect of the microphone air cavity, notably the width, shape and venting in the acquisition of sound spectra and the use of a single electret with a variety of plastic coupler.

Respiratory diseases are often characterized by multiple clinical signs or symptoms, for instance abnormal chest sound associated with increased respiratory rate and fever. It is known that the screening of respiratory disease is improved if several physiological parameters such as blood oxygen saturation are taken into account to diagnose the disease and determine its severity. During auscultation, physician generally uses a specific tool to evaluate each symptom separately which could be time consuming and could significantly negatively impact the efficiency of the diagnosis.

Overall, when it comes to acquire multiple parameters in a patient in an efficient manner, notably time efficient manner, and reliable manner, the existing stethoscopes do not provide satisfying solutions. One of the reasons is that the existing stethoscopes do not allow to record or monitor several parameters in a reliable and time efficient manner.

SUMMARY OF THE INVENTION

The above problems are solved by the device and the method according to the present invention.

In a first aspect, the invention concerns a device for measuring at least one parameter of a patient, the device comprising a casing equipped with at least one sensor for measuring said parameter of the patient, characterized in that the device comprises at least three sensors, each sensor being configured for measuring one distinct parameter, said three sensors being chosen among a list comprising at least a temperature sensor to measure a temperature of the patient, a sound sensor to record a body sound of the patient, preferably pulmonary sound and/or heart sound, and an oximeter sensor to measure an oxygen blood level of the patient and/or the patient's heart rate, said three sensors being mounted in the casing so that when the device is in contact with the skin of the patient, at least two distinct parameters, preferably three distinct parameters, are measured simultaneously.

In a second aspect, the invention concerns a method for measuring at least three parameters of a patient by using a device according to the present invention, the method comprising:

i) Contacting the device with the patient's chest skin;
ii) measuring the temperature of the patient and simultaneously recording the body sound of the patient;
iii) measuring the oximetry of the patient, characterized in that step i) and step ii) are performed simultaneously or one after another.

In a third aspect, the invention relates to a computer implemented method for remotely operating a device according to the present invention, the method comprising:

i) Providing a device according to the present invention;
ii) Connecting the device to a control unit arranged for controlling said device;
iii) Sending an activation signal from the control unit to the device to activate the sensors of the device and measure at least two distinct parameters of the patient, preferably three distinct parameters when the device is contacting the patient's skin;
iv) Connecting the control unit to a computation unit configured to process said parameters by applying mathematical tools;
v) Sending a transfer signal from the control unit to the device to transfer the measured parameter from the device to the server via the computation unit;
vi) Sending a processing signal from the control unit to the computation unit to process the transferred measured parameters to provide an output;
v) Upon completion of the parameter's processing by the computation unit, sending a feedback request to transfer the output from the computation unit to the control unit;

In a fourth aspect the invention relates to an apparatus, for instance computer device such as a smartphone or another mobile device, comprising means for carrying out the computer implemented method according to the present invention.

In a fifth aspect the invention concerns a computer program, for instance a software executed on a smartphone or mobile device, comprising instructions which, when the program is executed by a computer, cause the computer to carry out the computer implemented method according to the present invention.

DESCRIPTION OF THE INVENTION

The invention concerns a device for measuring at least one parameter of a patient, the device comprising a casing equipped with at least one sensor for measuring said parameter of the patient, characterized in that the device comprises at least three sensors, each sensor being configured for measuring one distinct parameter, said three sensors being chosen among a list comprising at least a temperature sensor to measure a temperature of the patient, a sound sensor to record a body sound of the patient, preferably pulmonary sound and/or heart sound, and an oximeter sensor to measure an oxygen blood level of the patient and/or the patient's heart rate, said three sensors being mounted in the casing so that when the device is in contact with the skin of the patient, at least two distinct parameters, preferably three distinct parameters, are measured simultaneously.

Advantageously, in the present invention, a plurality of parameters is acquired simultaneously in the patient. This allows to reduce the steps needed to measure several parameters in a patient and to improve diagnostic reliability and disease severity grading.

Overall, the present invention addresses the time or duration required to diagnose a disease, in particular a respiratory disease, by reducing the duration required to acquire relevant parameter's measurements.

Advantageously, measuring simultaneously the body sound, for instance lung and heart sound, the blood oxygen saturation, patient the patient heart rate and/or respiratory rate, and the body temperature will greatly improve the classification and the severity of diseases. Computing all these parameters simultaneously offer a diagnostic advantage over multiple parameters measured at different time points A disease is rarely characterised by only one feature like fever or increased respiratory rate or lung sound. Combining several features allows the distinction between different diseases, thus improves the precision of the diagnosis and the quality of care.

In a preferred embodiment, the temperature sensor and the pulmonary sensors operate simultaneously to measure respectively the body temperature and the pulmonary sound of the patient simultaneously.

In the present invention, at least three sensors are mounted in the casing so that at least two distinct parameters are measured simultaneously when the device is in contact with the skin of the patient. In other words, the position of the sensors with respect to the casing is chosen to allow simultaneous measurements of at least two parameters.

In a preferred embodiment, the casing comprises at least two externals, preferably opposite, faces namely a first main face and a second face, the first face comprising at least one sensor, preferably the oximeter sensor, and the second face comprising at least two sensors, preferably the temperature sensor and the sound sensor.

In a preferred embodiment, three sensors are mounted in the casing so that when the device is in contact with the skin of the patient, the temperature sensor, the sound sensor and the oximeter sensor operate simultaneously so that at least the temperature of the patient, the body sound of the patient and the oxygen blood level of the patient and/or the patient's heart rate are measured simultaneously. Thus, the three sensors are mounted in the casing to allow a simultaneous measurements of three distinct parameters, each acquired by one sensor.

In a preferred embodiment, the oximeter sensor is a reflection pulse oximeter. Contrary to transmission pulse oximeter which must be adapted to the morphology of the finger, reflection pulse oximeter it can be adapted to all finger morphologies. Thus, it is not necessary to change the measuring head of the oximeter. This allows to have a more compact and ergonomic device.

Preferably, the oximeter is configured for contacting the patient finger. This allows to place the oximeter on a face of the device which is not in contact with the patient's chest.

In a preferred embodiment, the oximeter is a reflection pulse oximeter placed on one main face of the device while the temperature sensor and the sound sensor are placed on the opposite main face of the device preferably configured for contacting the patient's chest, for instance circular main faces. Thus, this particular design allows to measure oximetry with the fingertip and measuring the breath sounds with the sensor placed on the chest at the same time, preferably these simultaneous measurements of the three parameters is done by the patient him/herself. This allows to measure three parameters in one step and to save time during the parameters acquisition.

Preferably, the sound sensor comprises body sensor, for instance a pulmonary and cardiac sensor, for recording body sound, for instance lung and heart sound, of the patient. The sound sensor further comprises an ambient sensor for recording ambient sound, or in other words cancelling ambient noise. The body sensor and the ambient sensor being configured for recording data simultaneously. The presence of the ambient sensor allows to filter or sort out the recorded pulmonary sound to discard noise or sound unrelated to the patient or not relevant for monitoring body sound. The ambient sensor measurement is correlated with the body sound measurement to improve the quality of the body sound, for instance pulmonary and cardiac sound, and thus their reading and interpretation.

Preferably, the pulmonary sensor comprises a resonance chamber designed for being coupled to a microphone, said chamber comprising a membrane configured for contacting the patient's skin. This configuration allows to optimize the acoustic transmission and to amplify the sound level in the desired frequency ranges.

Preferably, the casing is a cylinder volume extending between the first main circular face and the second main circular face, the first face comprising at least one sensor, preferably the oximeter sensor, and the second face comprising at least two sensors, preferably the temperature sensor and the sound sensor. The overall cylinder shaped provides a device that is easy to handle for the user. The cylinder casing can be handled in secure manner in the hand of the user.

Preferably, the oximeter sensor comprises an optical sensor configured for measuring oximetry upon contact with the patient's skin, preferably the patient's finger.

In a preferred embodiment, the oximeter sensor is received in an opening, preferably a blind hole, arranged in the first main face of the device so that when a finger of the patient is inserted or placed in front the opening, said finger contacts the oximeter sensor to allow an oximetry measurement. This configuration allows to adapt to all the morphologies of fingers and facilitates its use by the patient.

In a preferred embodiment, the device comprises at least five sensors, said sensors comprising

- a body sensor for recording body sound of the patient and
  - an ambient sensor for recording ambient noise; and
- a first temperature sensor and second temperature sensor,
- an oximeter sensor, preferably a reflection pulse oximeter.

The combination of these five sensors makes allows to optimize the parameters which are acquired on the patient compared to a device comprising three sensors. This allows to improve the reliability and the quality of the data acquired.

Using two sound sensors, for instance two microphones, allows to make an active noise reduction and thus improves the quality of the audio signal. For instance, the microphone recording lung sounds is integrated into a sound box equipped with a membrane. This configuration improves acoustic transmission between the patient's skin and the microphone.

Using two temperature sensors allows a differential temperature measurement of the patient. In other words, measuring the temperature in two points of contact allows a more precise and reliable measurement. The sensors are preferably located on the face of the device comprising the sound sensor(s), which makes it possible to record body sounds and measure the temperature simultaneously upon contacting the patient's skin.

Preferably, the device further comprises a memory for saving at least one measure of each parameter.

Preferably, the body sound comprises sound measurements recorded at various locations on the patient skin, for instance from two to ten locations, in particular from four to ten locations, for example from six to eight locations. Recording sound at multiple locations allow to better localize a disease in a specific location, for instance specific location of the lung or the heart, or inform if the disease involves the entire organ.

In a preferred embodiment, the device is a stethoscope.

In another aspect, the invention concerns a method for measuring at least three parameters of a patient by using a device according to the invention, the method comprising:

i) Contacting the device with the patient's chest skin;

ii) measuring the temperature of the patient and simultaneously recording the body sound of the patient;

iii) measuring the oximetry of the patient, and preferably the heart rate, characterized in that step i) and step ii) are performed simultaneously or one after another.

The particular advantages of the method are similar to the ones of the device according to the invention and will thus not be repeated here.

In another aspect, the invention relates to a computer implemented method for remotely operating a device according to the invention, the method comprising:

i) Providing a device according to the invention;

ii) Connecting the device to a control unit arranged for controlling said device;

iii) Sending an activation signal from the control unit to the device to activate the sensors of the device and measure at least two distinct parameters of the patient, preferably three distinct parameters when the device is contacting the patient's skin;

iv) Connecting the control unit to a computation unit configured to process said parameters by applying mathematical tools;

v) Sending a transfer signal from the control unit to the device to transfer the measured parameter from the device to the computation unit via the control unit;

vi) Sending a processing signal from the control unit to the computation unit to process the transferred measured parameters to provide an output;

vii) Upon completion of the parameter's processing by the computation unit, sending a feedback request to transfer the output from the computation unit to the control unit.

Advantageously, the device according to the present invention can be controlled or operated in a remote manner by a control unit. For instance, the control unit comprises electronic component to execute a program to control the device.

The control unit is connected on the one hand with the device and on the other hand with a server or another storage component. The signals emitted by the control unit allow to control the device notably to ensure the transfer of the parameter's measurements from the device to the server.

In another aspect, the invention relates to an apparatus, for instance computer device such as a smartphone, comprising means for carrying out the method according to the invention.

In another aspect, the invention relates to a computer program comprising instructions which, when the program is executed by a computer, cause the computer to carry out the method of the invention.

The embodiments describe for the device also apply to the methods and program according to the present invention mutatis mutandis and vice versa.

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

Figure 1:
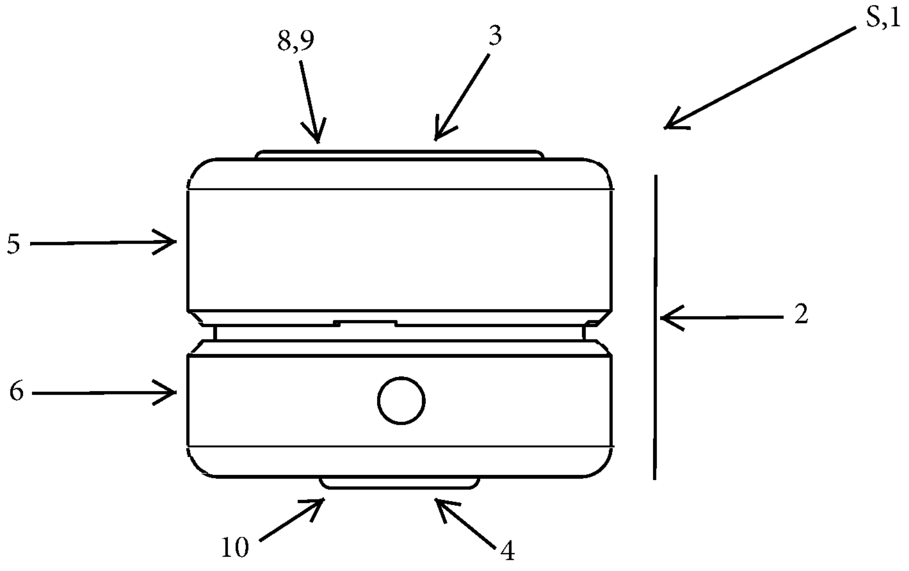
FIGS. 1 to 3 are a general overview of a device according to a first embodiment.
Figure 2:
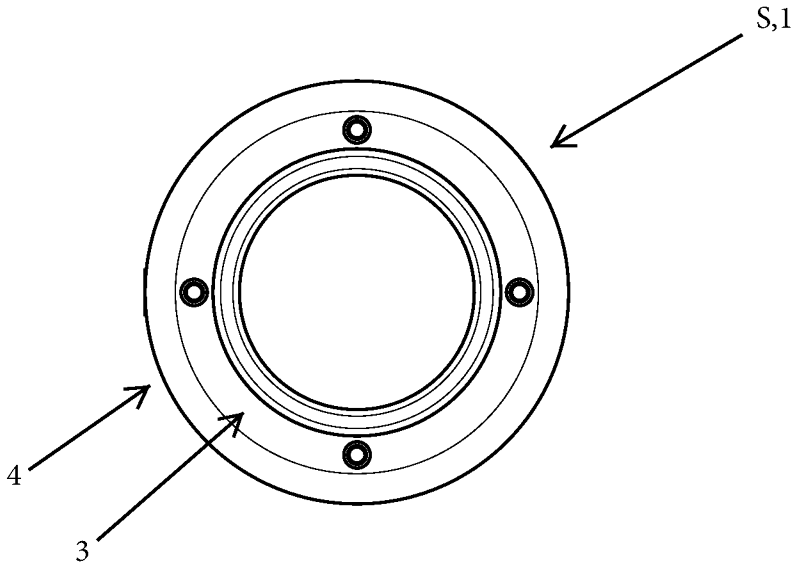
Figure 3:
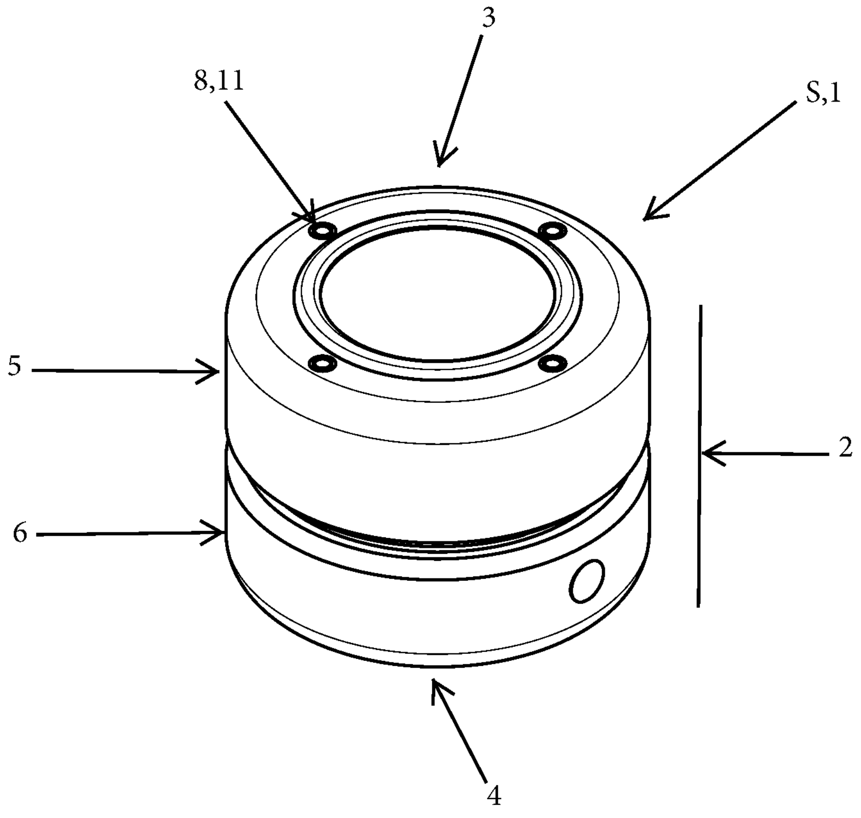

The present detailed description is intended to illustrate the invention in a non-limitative manner since any feature of an embodiment may be combined with any other feature of a different embodiment in an advantageous manner.

FIGS. 1 to 4 represent a device 1 according to a first embodiment of the present invention but the invention is not limited to this first embodiment.

The device 1 represented on the figures comprises is a stethoscope S comprising a casing 2 shaped as a cylinder volume extending between a first main circular face 3 and a second main circular face 4 opposite the first main circular face 3. The casing 2 is divided in two parts namely a cover 5 and body 6, the being fitted or embedded in the cover 5. In other words, the body 6 could be considered as the lower part of the casing 2 comprising the first main circular face 3 whereas the cover 5 is the upper part of the casing 2 comprising the second main circular face 4. For instance, the cover 5 is fixed to the body 6 by using a bayonet locking system.

In the embodiment represented on FIGS. 1 to 4, the casing has the following dimensions:

Height (between the first main circular face 3 and the second main circular face 4): 40 mm Width (as the diameter of the first main circular face 3 and the second main circular face 4)=54 mm The device 1 comprises three sensors, namely a temperature sensor 8, a sound sensor 9 and an oximeter sensor 10.

Figure 4:
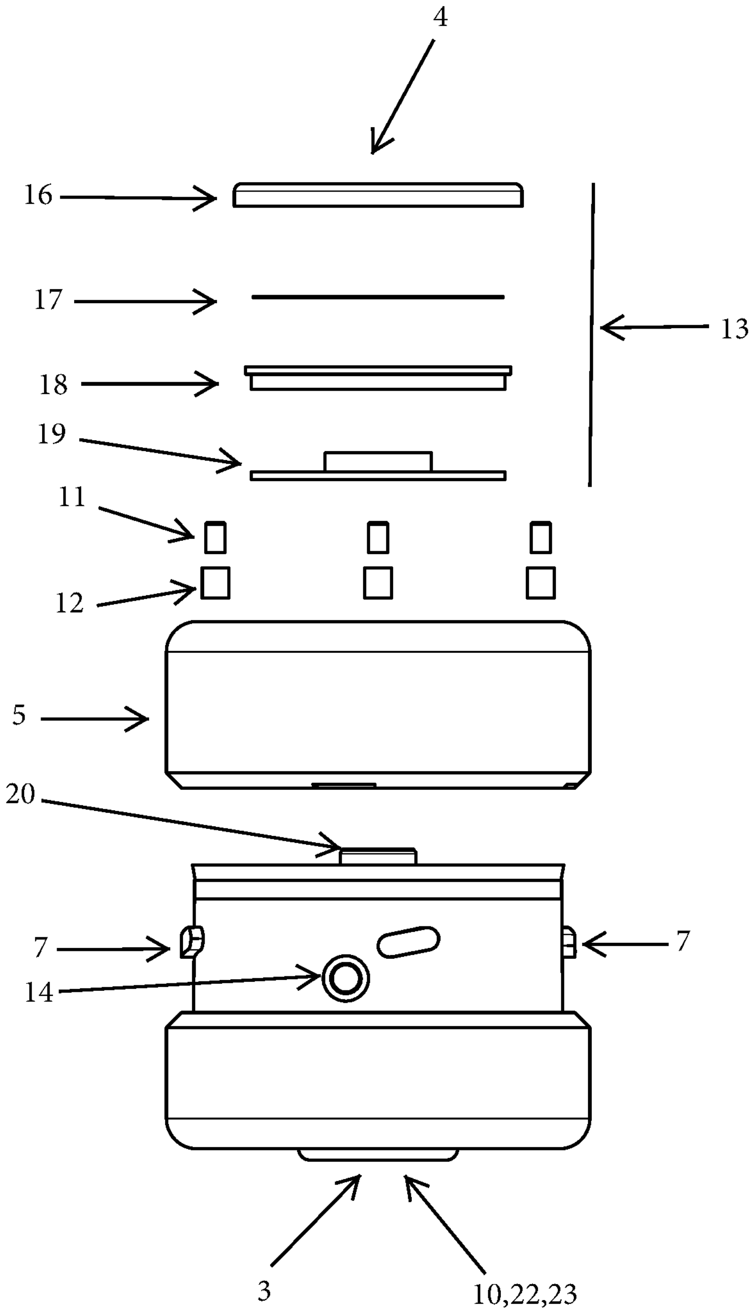
FIG. 4 is a detailed view of the device of FIGS. 1 to 3.

The temperature sensor 8 comprises four thermocouples 11 placed on the first main circular face 3. Each thermocouple 11 is coupled with a thermal insulation 12 as shown in FIG. 4.

The sound sensor 9 comprises a body sensor 13 for recording body sound of the patient and an ambient sensor 14 for recording ambient noise, the body sensor 13 and the ambient sensor 14 being configured for recording data simultaneously.

the body sensor 13 in the present embodiment is configured for recording pulmonary sound but in other embodiment (not shown here), the body sensor 13 is configured for recording pulmonary sound and cardiac sound.

The body sensor 13 comprises an ensemble of circular elements 15 embedded one another toward the first main circular face 3, said ensemble comprising:

A diaphragm holder 16;

A diaphragm (or a membrane) 17;

A resonance chamber 18

An acoustic insulation 19;

The ensemble of circular element 15 is further coupled to a first microphone 20 whereas the ambient sensor comprises a second microphone 21 for recording ambient noise.

The oximeter sensor 10 the oximeter sensor is received in an opening 22, here a blind hole 23, arranged in the first main face 3 of the device 1. An optical sensor 24 is placed in the bottom of the blind hole 23 (not shown in FIG. 4) so that when a finger of the patient is inserted in the opening 22 and reaches the bottom of the blind hole 23, the finger contacts the optical sensor 24 to allow an oximetry measurement.

The three sensors of the device 1 are mounted in the casing 1 so that when the device 1 is in contact with the skin of the patient, two distinct parameters namely the body sound and the temperature are measured simultaneously:

The temperature sensor 8 and the sound sensor 9 (via the diaphragm 17) are placed on the first main circular face 3 of the device and are contacting the skin of the patient simultaneously;

The oximeter sensor 10 is placed on the second main circular face 4.

In this embodiment, the design of the device 1 has been developed so that the user can hold it in one hand to perform the measurement of body sound and temperature simultaneously. The oximetry measurement is carried out in a second step by placing the finger in the housing provided for this purpose.

However, the invention is not limited to the configuration and locations of sensors as represented on FIGS. 1 to 4. The invention concerns any alternative configurations or locations of the sensors where the three sensors are mounted in the casing (2) so that when the device (1) is in contact with the skin of the patient, at least two distinct parameters, preferably three distinct parameters, are measured simultaneously.

Figure 5:
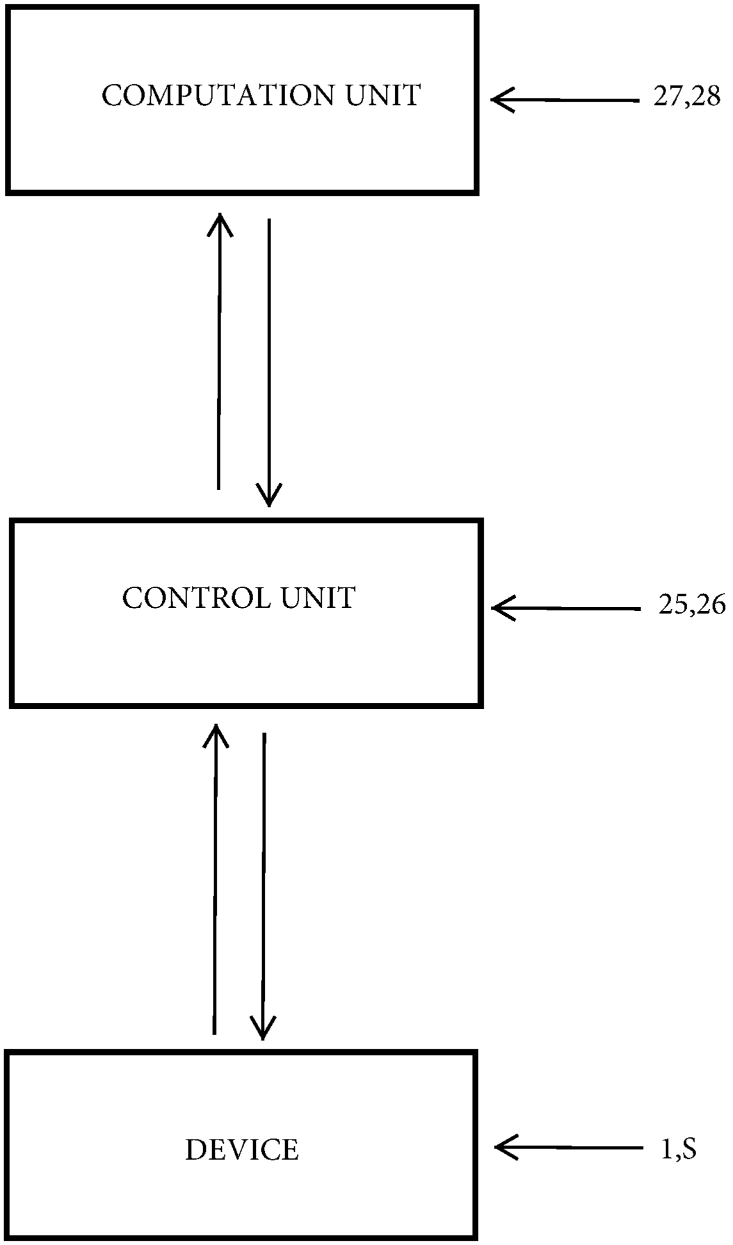
FIG. 5 is a scheme representing an embodiment of the computer implemented method according to the present invention.

FIG. 5 illustrates the computer implemented method according to the invention where the device 1 is connected to a control unit 25, for instance a smartphone 26 that is further connected to a computation unit 27 located for instance on a sever 28. The smartphone 28 may comprised a computer program, for instance an application or another software, and the software, when executed, is configured for controlling in a remote manner the device 1.

An example of the computer implemented method is described below and represented in FIG. 5:

Connecting the device 1 to the smartphone 26 arranged for controlling said device, for instance by pairing the smartphone with the device notably via Bluetooth communication protocol;

Executing the application on the smartphone to send an activation signal to the device to activate the sensors of the device 1 and measure at least two distinct parameters of the patient, preferably three distinct parameters when the device 1 is contacting the patient's skin; for instance, activating the temperature sensor 8 and the sound sensor 9;

Storing the measured parameters on the internal memory of the smartphone 26;

Connecting the smartphone 26 to the computation unit 27 located on the server 28 and configured to process said parameters by applying mathematical tools;

Sending a transfer signal from the application executed on the smartphone 26 to the device 1 to transfer the measured parameter from the device 1 to the server 28 via the smartphone 26;

Sending a processing signal from the application executed on the smartphone 26 to the computation unit 28 to process the transferred measured parameters to provide an output;

Upon completion of the parameter's processing by the computation unit 28, sending a feedback request from the application executed on the smartphone 26 to the computation unit 27 to transfer the output from the computation unit 28 to the smartphone.

The output provided by the method according to the present invention allows to or are taken into account to diagnose a disease. Advantageously, it allows to or is taken into account to determine the severity of the disease.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This for example particularly the case regarding the different apparatuses which can be used.

REFERENCE NUMBERS

1 Device according to a first embodiment
S Stethoscope
2 Cylinder casing
3 First main circular face
4 Second main circular face
5 Cover
6 Body
7 Bayonet locking system
8 Temperature sensor
9 Sound sensor
10 Oximeter sensor
11 Thermocouple
12 Thermal insulation
13 Body sensor
14 Ambient sensor
15 Ensemble of circular elements
16 Diaphragm holder
17 Diaphragm
18 Resonance chamber
19 Acoustic insulation
20 First microphone
21 Second microphone
22 Opening
23 Blind hole
24 Optical sensor
25 Control unit
26 Smartphone
27 Computation unit
28 Server

The invention claimed is:

1. A device comprising a casing equipped with at least three sensors, each sensor being configured for measuring one distinct parameter of the patient, said three sensors are respectively a temperature sensor to measure a temperature of the patient, a sound sensor to record a body sound of the patient, and an oximeter sensor to measure an oxygen blood level of the patient and/or the patient's heart rate, said three sensors being mounted in the casing so that when the device is in contact with the skin of the patient, the at least the three sensors measure the at least three distinct parameters simultaneously, characterized in that the casing comprises two opposite externals faces namely a first main face and a second main face, the first main face comprising at least the oximeter sensor, and the second main face comprising at least the temperature sensor and the sound sensor.

2. The device according to claim 1, wherein the sound sensor comprises a body sensor for recording body sound of the patient and an ambient sensor for recording ambient noise, the body sensor and the ambient sensor being configured for recording data simultaneously.

3. The device according to claim 2, wherein the body sensor comprises a resonance chamber designed for being coupled to a microphone, said resonance chamber comprising a membrane configured for contacting the patient's skin.

4. The device according to claim 1, wherein the casing is a cylinder volume extending between the first main face and the second main face, wherein the first main face and second main face are both circular.

5. The device according to claim 4, wherein the oximeter sensor is received in an opening, arranged in the first main face of the device so that when a finger of the patient is inserted in the opening, said finger contacts the oximeter sensor to allow an oximetry measurement.

6. The device according to claim 4, wherein the oximeter is a reflection pulse oximeter placed on one the main circular face of the device while the temperature sensor and the sound sensor are placed on the opposite circular main face of the device.

7. The device according to claim 1, wherein the oximeter sensor comprises an optical sensor configured for measuring oximetry upon contact with the patient's skin.

8. The device according to claim 1, wherein the device comprises at least five sensors, said sensors comprising:

a body sensor for recording body sound of the patient and an ambient sensor for recording ambient noise;

a first temperature sensor and second temperature sensor; and the oximeter sensor.

9. The device according to claim 1, wherein the device further comprises a memory for saving at least one measure of each parameter.

10. The device according to claim 1, wherein the sound sensor is a stethoscope.

11. A method for measuring at least three parameters of a patient by using a device according claim 1, the method comprising-:

i) contacting the device with the patient's chest skin;

ii) measuring the temperature of the patient and simultaneously recording the body sound of the patient;

iii) measuring the oximetry of the patient, characterized in that step i) to iii) are performed simultaneously.

12. The method according to claim 11, wherein the body sound comprises sound measurements recorded at more than one location on the patient's skin.

13. A method for remotely operating a device according to claim 1, the method comprising:

i) connecting the device to a control unit arranged for controlling said device;

ii) sending an activation signal from the control unit to the device to activate the sensors of the device and measure at least two distinct parameters of the patient;

iii) connecting the control unit to a computation unit configured to process said parameters by applying mathematical tools; and wherein the method further comprises a computer implemented method comprising the following steps:

iv) sending a transfer signal from the control unit to the device to transfer the measured parameter from the device to the computation unit via the control unit;

v) sending a processing signal from the control unit to the computation unit to process the transferred measured parameters to provide an output; and vi) upon completion of the parameter's processing by the computation unit, sending a feedback request to transfer the output from the computation unit to the control unit.

14. The method of claim 13 wherein the control unit is a smartphone.

15. A non-transitory computer-readable medium storing instructions that cause performance of steps iv)-vi) of claim 13 when executed by a computation unit.

* * * * *